US006281242B1

(12) United States Patent
Regan et al.

(10) Patent No.: US 6,281,242 B1
(45) Date of Patent: Aug. 28, 2001

(54) PROPHYLACTIC OR THERAPEUTIC AGENT FOR AMNESIA

(75) Inventors: Ciaran Regan; David O'Gorman, both of Dublin; Alan O'Connell, Offaly, all of (IE); Tadashi Shiotani, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/462,099

(22) PCT Filed: Jul. 14, 1998

(86) PCT No.: PCT/JP98/03162

§ 371 Date: Jun. 2, 2000

§ 102(e) Date: Jun. 2, 2000

(87) PCT Pub. No.: WO99/03466

PCT Pub. Date: Jan. 28, 1999

(30) Foreign Application Priority Data

Jul. 15, 1997 (JP) ................................................ 8/189495

(51) Int. Cl.$^7$ .................................................... A61K 31/40
(52) U.S. Cl. ............................................................ 514/424
(58) Field of Search ............................................. 514/424

(56) References Cited

U.S. PATENT DOCUMENTS

| 4,341,790 | 7/1982 | Betzing et al. ...................... 514/424 |
| 5,461,157 | 10/1995 | Kamihara et al. ................... 548/550 |
| 5,886,023 | 3/1999 | Otomo et al. ........................ 514/424 |
| 5,996,023 | * 3/1999 | Otomo et al. ........................ 514/424 |
| 6,107,330 | * 8/2000 | Nabeshima et al. ................. 514/424 |

FOREIGN PATENT DOCUMENTS

| 56-2960 | 1/1981 | (JP) . |
| 5-163144 | 6/1993 | (JP) . |
| 5-163145 | 6/1993 | (JP) . |

OTHER PUBLICATIONS

Hiramatsu et al., "Involvement of the cholinergic system in the effects of nefiracetam (DM–9384) on carbon monoxide (CO)–induced acute and delayed amnesia", Eur. J. Pharmacol., vol. 216, No. 2, pp. 279–285 (1992).

Nabeshima et al., "Effects of DM–9384, a Cyclic Derivative of GABA, on Amnesia and Decreased in $GABA_A$ and Muscarinic Receptors Induced by Cycloheximide", J. Pharmoc. Exp. Ther., vol. 257, No. 1, pp. 271–275 (1991).

Nabeshimi et al., "Effects of DM–9384, a Pyrrolidone Derivative, on Alcohol– and Chlordiazepoxide–Induced Amnesia in Mice", Pharmoc. Biochem. Behav., vol. 36, No. 2, pp. 233–236 (1990).

Ogg, "Today's Treatment, Use of Anaesthesia, Implications of day–case surgery and Anaesthesia", Brit. Med. J., 281, pp. 212–214 (1980).

Ogg, "Today's Treatment, Use of Anaesthesia, Implications of day–case surgery and Anaesthesia", Brit. Med. J., 281, pp. 212–214 (1980).

Nobel et al., "The Effect of Propofol ('Diprivan') and Methohexitone on Memory after day case Anaesthesia (Abstract)" Postgrad. Med., J., 61, pp. 103–104 (1985).

Pang et al., "Effect of Propofol on Memory in Mice", Pharmacol. Biochem. Behav., 44, pp. 145–151 (1993).

Steib et al., "Recovery from Total Intravenous Anaesthesia. Propofol versus Midazolam–Flumazenil", Acta Anethesiol Scand., 34, pp. 632–635 (1990).

Bethune et al., "Learning During General Anaesthesia: Implicit Recall after Methohexitone or Propofol Infusion", Brit J. Anaesthesia, 69, pp. 197–199 (1992).

Cork et al., "Is there Implicit Memory after Propofol Sedation?", Brit. J. Anaesthesia, 76, pp. 492–498 (1996).

Sanou et al., "Cognitive Sequelae of Propofol Anaesthesia", Neuro Report, 7, pp. 1130–1132 (1996).

Ghouri, "Effect of Flumazenil of Recovery Midazolam and Propofol Sedation", Anesthesiology, 81, pp. 333–339 (1994).

Mondadori et al., "Delayed Emergence of Effects of Memory–Enhancing Drugs: Implications for the Dynamics of Long–term Memory", Proc. Natl. Acad. Sci., USA, 91, pp. 2041–2045 (1994).

Mondadori et al., "Do Piracetam–like Compounds act Centrally via Peripheral Mechanisms?", Brain Res., 435, pp. 310–314 (1987).

Doyle et al., "Nefiracetam (DM–9384) Preserves Hippocampal Neural Cell Adhesion Molecule–Mediated Memory Consolidation Processes During Scopolamine Disruption of Passive Avoidance Training in the Rat?", J. Neurochem., 61, pp. 266–272 (1993).

Fox et al., "Memory Consolidation induces a Transient and Time–Dependent Increase in the Frequency of Neural Cell Adhesion Molecule Polysialylated Cells in the Adult Rat Hippocampus", J. Neurochem., 65, pp. 2796–2799 (1995).

Murphy et al., "Repetitive and Transient Increases in Hippocampal Neural Cell Adhesion Molecule Polysialylation State Following Multitrial Spatial Training", J. Neurochem., 67, pp. 1268–1274 (1996).

(List continued on next page.)

Primary Examiner—James H. Reamer
(74) Attorney, Agent, or Firm—Greenblum & Bernstein, P.L.C.

(57) ABSTRACT

A medicament comprising as an active ingredient a compound represented by the following formula: $R^2$—$CH_2CONH$—$R^1$ wherein $R^1$ represents pyridyl group, a substituted pyridyl group, phenyl group, or a substituted phenyl group; and $R^2$ represents a 2-oxo-1-phyrrolidinyl group which may be substituted (e.g., N-(2,6-dimethylphenyl)-2-(2-oxo-1-pyrrolidinyl)acetamide), which is useful for preventive and/or therapeutic treatment of amnesia caused by, for example, an anesthetic agent for intravenous administration such as propofol.

18 Claims, No Drawings

OTHER PUBLICATIONS

Odumeru et al., "Influence of Nefiracetam on NGF–Induced Neuritogenesis and Neural Cell Adhesion Molecule Polysialic Acid Expression: In Vivo and In Vitro Comparisons", Behav. Brain Res., 83, pp. 173–178 (1997).

Bailey et al., "Structural Changes Accompanying Memory Storage", Annu. Rev. Physiol., 55, pp. 397–426 (1993).

Kitano et al., "General Pharmacological Profile of the New Cognition–Enhancing Agent Nefiracetam", Arzneim.–Forsch./Drug Res. 44(I), Nr. 2a, pp. 199–210 (1994).

Ogg et al., "Day Case Anaesthesia and Memory", Anaesthesia, 34, pp. 784–789 (1979).

Yamada et al., "Nefiracetam (DM–9384): A Novel Antiamnesic Drug", CNS Drug Reviews, vol. 2, No. 3, pp. 322–342 (1996).

Hiramatsu et al, Behav. Brain Res., vol. 83, #1–2, pp. 107–115 (abstract), Feb. 1997.*

Doyle et al, Neurochem. Res., vol. 21, #6, pp. 649–652 (abstract), Jun. 1996.*

Shiotani et al, J. Neutral Transm. Gen. Sect., vol. 90, #2, pp. 103–111 (abstract), Feb. 1992.*

Nabeshima et al, Eur. J. Pharmacol, vol. 20, #2, pp. 143–149 (abstract), Mar. 1990.*

* cited by examiner

PROPHYLACTIC OR THERAPEUTIC AGENT FOR AMNESIA

This application is a 371 of PCT/JP98/03162 filed Jul. 14, 1998.

BACKGROUND OF THE INVENTION

1. Field of the Invention

The present invention relates to medicaments. More specifically, the present invention relates to medicaments which comprises as an active ingredient 2-(1-pyrrolidinyl) acetamide derivatives, whose typical example includes neifracetam, and is useful for preventive and/or therapeutic treatment of amnesia caused by general anesthesia and the like.

2. Discussion of the Background Information

In emergency anesthesia, which accounts for 70% of all anesthesia used for surgical operations, certain and rapid recovery from anesthesia is desired for safety of a patient (Korttila, K., et al., Acta Anaesthesiol. Scand., 34, pp. 400–403, 1990; Ogg, T. W., Brit, Med. J., 281, pp. 212–214, 1980; Noble, J., et al., Postgrad. Med., J., 61, pp. 103–104, 1985). Progress has been made in development of anesthetic agents that are rapidly metabolized and leave only slight hangover effects. However, there still remains a problem of significant cognitive disorders immediately after operations.

For example, propofol (diisopropylphenol; Diprivan) is a short-time acting intravenous anesthetic agent that has been preferably used because of its fast and smooth anesthesia induction and rapid recovery. However, it has been suggested that propofol may possibly cause amnesia at wakening from anesthesia. Effects of propofol on memory formation have not fully revealed to date. In rodents, subanesthetic doses of propofol were demonstrated to induce anterograde amnesia as for avoidance tasks, whilst similar dose ranges failed to induce retrograde amnesia (Pang, R. et al., Pharmacol. Biochem. Behva., 44, pp. 145–151, 1993; a possible interpretation of these results is that retrograde amnesia was not observed because of the maximum dose of 100 mg/kg after training). Contrary to these results, the inventors of the present invention found that retrograde amnesia was also induced by administration of a higher dose of propofol (see, examples given in the present specification).

As for amnesia in human, propofol has been suggested to induce anterograde amnesia of intraoperative events (Steib, A. et al., Acta Anaesthesiol. Scand., 34, pp. 632–635, 1990). However, there is still debate as to whether it affects cryptomnesia (Bethune, D. W., et al., Brit. J. Anaesthesia, 69, pp. 197–199, 1992; and Cork, R. C., et al., Br. J. Anaesthesia, 76, pp. 492–498, 1996). In addition, it has also been reported that cognitive functions associated with learning, language, reasoning, and planning remain suppressed for at least 3 hours after cessation of propofol administration (Sanou, J., et al., Neuro Report, 7, pp. 1130–1132, 1996).

Agents that assist recovery from the cognitive disorders associated with propofol-induced anesthesia are expected as clinically useful; however, only a few agents have so far been known (Ogg, T. W., et al., Anaesthesia, 34, pp. 783–789, 1979; Ghouri, A., Anesthesiology, 81, pp. 333–339, 1994). For example, doxapram and flumazenil have been investigated. However, these medicaments have not been generally used due to a possible risk of re-sedation arising from the short acting nature of these agents.

2-(1-Pyrrolindinyl)acetamide derivatives have been known to exhibit improving effects on cerebral function (Japanese Patent Application Unexamined Publication (Kokai) No. 56-2960/1981). In particular, N-(2,6-dimethylphenyl)-2-(2-oxo-1-pyrrolidinyl)acetamide (generic name: nefiracetam) has been revealed to have clinical usefulness as a cerebral function improving agent. Nefiracetam has been known to preserve memory formation in various animals models of learning disability (Yamada, K., et al., CNS Drug Reviews, 2, pp. 322–342, 1996).

The class of cognition-enhancing agents including nefiracetam as a typical example require 16 to 24 hours before their memory improving effects are exhibited (Mondadori, C., et al., Proc. Natl. Acad. Sci., USA, 91, pp. 2041–2045, 1994). Since these agents are ineffective in adrenalectomised animals, it has been suggested that they regulate gene transcription in such a manner that formation of long term memory trace is facilitated (Mondodori, C., et al., Brain Res., 435, pp. 310–314, 1987). The regulatory ability has been demonstrated in adult rats by evaluating the ability of nefiracetam to protect scopolamine-compromised learning-dependent modifications of nerve cell adhesive molecule (NCAM) in a polysialylation state, which occur in the memory fixation period 10 to 12 hours after training in a certain population of granular cells at the boundary hilus of dentate gyrus granule cell layer (Doyle, E., et al., J. Neurochem., 61, pp. 266–272, 1993; Fox, G. B. et al., J. Neurochem., 65, pp. 2796–2799, 1995; and Murphy, K. J., et al., J. Neurochem., 67, pp. 1268, 1274, 1996).

A similar effect has been observed in an in vitro experiment using a PC-12 pheochromocytoma cell model. Pre-exposure to Nefiracetam of sensitized PC-12 cells significantly enhances subsequent nerve growth factor-induced neuritogenesis and NCAM polysialylation (Odumeru, O., et al., Behav. Brain Res., 83, pp. 173–178, 1997). While this action is not apparent dose-dependent, it is considered that nefiracetam enhances time-dependent regulation of neuro-plasticization events after training, and thereby contributes to the synaptic rearrangements underlying the memory fixation (Bailey, C. H., Annu. Rev. Physiol., 55, pp. 397–426, 1993).

SUMMARY OF THE INVENTION

An object of the present invention is to provide a medicament for preventive and/or therapeutic treatment of amnesia. More specifically, the object of the present invention is to provide a medicament for preventive and/or therapeutic treatment of amnesia that is caused by general anesthesia induced by use of an anesthetic agent such as propofol, and onsets after awaking from the general anesthesia.

The inventors of the present invention conducted various studies to achieve the foregoing object, and as a result, they found that 2-(1-pyrrolidinyl)acetamide derivatives known as useful agents for cerebral function improvement, in particular nefiracetam, remarkably suppressed amnesia after awaking from general anesthesia. The present invention was achieved on the basis of these findings.

The present invention thus provides a medicament for preventive and/or therapeutic treatment of amnesia, which comprises as an active ingredient a compound represented by the following formula (I): $R^2$—$CH_2CONH$—$R^1$ (I) wherein $R^1$ represents pyridyl group, a substituted pyridyl group, phenyl group, or a substituted phenyl group; and $R^2$ represents a 2-oxo-I-pyrrolidinyl group which may be substituted, preferably comprises nefiracetam.

According to preferred embodiments of the present invention, there are provided the aforementioned medicament for preventive and/or therapeutic treatment, which is used for amnesia caused by general anesthesia; the aforementioned medicament for preventive and/or therapeutic treatment, which is used for amnesia that occurs after awaking from general anesthesia; the aforementioned medicament for preventive and/or therapeutic treatment, wherein the amnesia is anterograde amnesia; the aforementioned medicament for preventive and/or therapeutic treatment, wherein the amnesia is retrograde amnesia; the aforementioned medicament of preventive and/or therapeutic treatment, wherein the general anesthesia is produced by an anesthetic agent for intravenous administration; and the aforementioned medicament for preventive and/or therapeutic treatment, which is in the form of a pharmaceutical composition comprising a compound of formula (I) as an active ingredient, preferably nefiracetam, together with an additive for pharmaceutical preparations. As further aspects of the present invention, there are provided a use of a compound of the formula (I), preferably, nefiracetam, for the manufacture of the aforementioned medicament for preventive and/or therapeutic treatment; and a method for prevention and/or therapeutic treatment of amnesia, which comprises the step of administering a preventively and/or therapeutically effective amount of a compound of the formula(I), preferably, nefiracetam, to a patient.

DETAILED DESCRIPTION OF THE PRESENT INVENTION

Best Modes for Carrying out the Invention

The active ingredients of the medicaments of the present invention, i.e., the 2-(1-pyrrolidinyl)acetamide derivatives, are described in Japanese Patent Application Unexamined Publication (Kokai) No. 56-2960/1981 as compounds useful for improving cerebral functions. $R^1$ represents pyridyl group, a substituted ppyridyl group, phenyl group, or a substituted phenyl group. Examples of the substituents present on the ring of the substituted pyridyl group or the substituted phenyl group include a halogen atom, trifluoromethyl group, nitro group, acetyl group, an alkyl group, an alkoxy group, an alkylmercapto group, amino group, sulfonyl group, aminoethoxy-carbonyl group and the like.

$R^2$ represents a 2-oxo-1-pyrrolidinly group which may be substituted. The substituent may be hydroxyl group and the like. The aforementioned compounds can easily be prepared, for example, according to the methods described in Japanese Patent Application Unexamined Publication (Kokai) Nos. 56-2960/1981, 6-65197/1994 and the like. Among them, most preferred compound is N-(2,6-dimethyl-phenyl)-2-(2-oxo-1-pyrrolidiny) acetamide which has been clinically used with a generic name of "nefiracetam".

The medicament of the present invention can be used for preventive and/or therapeutic treatment of amnesia which includes both of anterograde amnesia and retrograde amnesia and either or both of them may preferably be treated by the medicament of the present invention. The term "anterograde amnesia" used herein refers to memory disorder for future events after the time of participation of amnesia-inducing factor (e.g., administration of general anesthetic agent), whereas the term "retrograde amnesia" refers to memory regeneration disorder for past events before the time of participation of amnesia-inducing factor. However, disease to be treated by a medicament of the present invention are not limited to these specific types of amnesia.

Amnesia has been known to be induced by general anesthesia, and the medicament of the present invention can preferably be used for preventive and/or therapeutic treatment of amnesia caused by general anaesthesia. The type of general anaesthesia is not particularly limited, and any type of anesthesia that may possibly induce amnesia may be treated. Examples of general anesthesia include inhalation anesthetics such as halothane, methoxyfluran and the like; intravenous anesthetics such as sodium thiopental, ketamine, propofol and the like; introduction anesthetics used along with inhalation anesthetics; and combinations thereof. Among them, anesthesia produced by a short-acting intravenous anesthetic such as propofol may preferably treated by the medicament of the present invention.

The administration route of the medicament of the present invention is not particularly limited, and it may be administered orally or parenterally. The active ingredients, i.e., the compounds of the formula (I), may be used per se as the medicament of the present invention. It is generally preferred that a pharmaceutical preparation in a form will known to those skilled in the art may be prepared by appropriately using one of more pharmacologically and pharmaceutically acceptable additives together with a compound of the formula (I), and administered orally or parenterally. As the active ingredients, physiologically acceptable salts of the compounds of the formula (I), as well as hydrates and solvates of the compounds in a free form of physiologically acceptable salts thereof may be used.

Examples of pharmaceutical preparations suitable for oral administration include, but are not limited to, tablets, capsules, powders, subtilized granules, granules, liquids, syrups and the like. Examples of pharmaceutical preparations suitable for parenteral administration include, but are not limited to, injections for subcutaneous, intravenous, or intramuscular injection, drip infusions, suppositories, inhalants, transdermal preparations, transmucosal preparations, patches and the like. Examples of pharmacologically and pharmaceutically acceptable additives include excipients, disintegrators or disintegrating aids, binders, lubricants, coating agents, colorants, diluents, base materials, dissolving agents or dissolving aids, isotonic agents, pH modifiers, stabilizers, propellants, adhesives and the like.

The preparations suitable for oral, transdermal, or transmucosal administration may be manufactured by using as pharmacologically and pharmaceutically acceptable additives, for example, excipients such as glucose, lactose, D-mannitol, starch and crystalline cellulose; disintegrators or disintegrating aids such as carboxymethylcellulose, starch and calcium carboxymethylcellulose binders such as hydroxypropylcellulose, hydroxypropylmethylcellulose, polyvinyl-pyrrolidone and gelatin; lubricants such as magnesium stearate and talc; coating agents such as hydroxyproplymethylcellulose, sucrose, polyethylene glycol and titanium oxide; and base materials such as vaseline, liquid paraffin, polyethylene glycol, gelatin, kaolin, glycerin, purified water and hard fat. In addition, the preparations may be manufactured by using propellants such as frons, diethylether and compressed gases; adhesive such as sodium polyacrylae, polyvinyl alcohol, methylcellulose, polyisobutyrene and polybutene; and substrates such as cotton cloths or plastic films.

Preparations suitable for injection or drip infusion may contain additives for pharmaceutical preparations such as, for example, dissolving agents or dissolving aids that can constitute aqueous injections or injections that are dissolved upon use such as distilled water for injections, physiological saline and propylene glycol; isotonic agents such as glucose, sodium chloride, D-mannitol and glycerin; pH modifiers such as inorganic acids, organic acids, inorganic bases and organic bases and the like.

A dose of the medicament of the present invention is not particularly limited, and it can be suitably determined depending on administration route, severity of amnesia, purpose of administration, i.e., preventive or therapeutic administration, age and body weight of a patient and so forth. Exemplary useful doses are within the range of 200 to 2,000 mg, preferably 300 to 900 mg, per day as the amount of the active ingredient, and the daily dose may be administered as two or more divided portions. Administration time or period of the medicament of the present invention may also be appropriately chosen. The medicament has been revealed to exhibit prophylactic effect against amnesia when administered before anesthesia (see, examples given below, Tables 3 and 4). Similar effects may be expected when the medicament of the present invention is administered after anesthesia.

EXAMPLES

The present invention will explained more specifically with reference to the following examples. However, the scope of the present invention is not limited to these examples.

In the following examples, N-(2,6-dimethylphenyl)-2-(2-oxo-1-pyrrolidinyl)-acetamide (generic name: nefiracetam, referred to as "nefiracetam" hereinafter in the examples) was used as the medicament of the present invention, and its effects on amnesia produced by propofol (diisopropylphenol), which is a short-time acting intravenous anesthetic, was evaluated. More specifically, anterograde and retrograde amnesia caused by subanesthetic and anesthetic doses of propofol were evaluated by determining regulation of NCAM polysialylation and rat memory regeneration in passive avoidance response task, and effect of nefiracetam on these two parameters were evaluated.

(1) Experiments (a) Passive avoidance training 80 day-old male Wistar rats (300–350 g) were individually caged under standard condition with food and water available ad libitum. The animals were introduced into the test environment 3 days before the start of the experiment and then maintained under the same condition. The passive avoidance model employed was a one-trial, step-through type, light-dark model. On the training day, each animal was evaluated for behavioral activity. Then, the animal was placed into the light compartment of the passive avoidance apparatus, and latency to enter the dark compartment was recorded: The animal was given with slight foot shock at 0.75 mA for 5 seconds immediately after it entered the dark compartment to have the animal immediately return to the light compartment to avoid the stimulus. In order to examine memory regeneration ability of each animal, the animals were placed in the light compartment 12 hours after the training, and the latency to enter the dark compartment was recorded. This value was used as an index of the ability of each animal to memorize the inhibitory stimulus (foot shock). The standard period for evaluation was 600 seconds.

In one experiment, the rat was intraperitoneally administered with propofol (Aldrich) dissolved in 0.9% physiological saline containing 10% Tween-20 (Sigma) 15 minutes before the training. In other experiments, the administration was performed at different times after the training. The depth of propofol-produced anesthesia in animals by a sole administration of propofol or combined administration with nefiracetam was determined based on loss of tail pinch reaction and pedal withdrawal reflex time. The expression time of righting reflex was used as in index of the time required for recovery from the anesthesia. Nefiracetam (Daiichi Pharmaceutical Co., Ltd.) was intraperitoneally administered 1 hour before the training. All experimental procedures were approved by the board of approval of Faculty of Biochemistry, University College of Dublin, and were carried out by individuals properly licensed by the Department of Health.

(b) Quantification of hippocampal polysialylated neurons

PSA (polysialic acid) immunocytes were measured by the method of Fox et al. (Fox, G. B. et al., J. Neurochem., 65, pp. 2796–2799, 1995) to detect hippocampal polysialylated neurons. Frozen axial sections of 12 $\mu$m were fixed in 70% (v/v) ethanol, and incubated overnight with with a 1:500 dilution of anti-polysialic acid and an ascitic fluid (kind gift from Prof. G. Rougon; Rougon, G. et al., J. Cell, Biol., 103, pp. 2429–2437, 1986). The sections here then exposed for 3 hours to a 1:100 dilution of fluorescein-conjugated goat anti-mouse IgM (Calbiochem), and inoculated on a flurrescence-enhancing medium, Citifluor (registered trademark, agar).

These sections were brought into contact with propidium iodide (40 ng/ml in PBS, Sigma Chemical, UK) for a short period (60 seconds) so as to counter-stain the nuclei with fluorescence. The total number of PSA-immunopositive neurons in the granule cell layer and boundary hilus were counted in ten 12 $\mu$m-sections commencing at −5.6 mm of the bregma, and double counting in the 5–10 $\mu$m perikarya was precluded. Cell number was divided by the total area of the granule cell layer, and multiplied by the average granular cell layer area (0.15±0.01 mm$^2$ at this level), and results of calculated mean±standard error were indicated as number of PSA-positive cells per unit area. Area measurement was performed by using a Quantimet 500 Image Analysis System.

(c) Statistical analysis

All of the values were expressed as mean ±standard error, and their statistical significance was determined by using the Mann-Whitney U=test for the behavioral data, and Student's t-test for the immunohistochemical data. Values of $p<0.05$ were accepted to be significant.

(2) Results

To determine whether or not propofol affected anterograde amnesia, the anesthetic was administered to the animals 15 minutes before the training for the passive avoidance response. All control animals were considered to sufficiently master the task as judged from the escape latencies determined 12 hours after the training and prior to sacrifice. In contrast, those administered with 75 mg/kg propofol were clearly with significant amnesia as evidenced by their shortened latencies to enter the dark compartment. The state amnesia was concluded as dose-dependent because there was no significant reduction in the latency at the lower dose of 10 mg/kg. The results are shown in Table 1. The latencies are expressed as mean±standard error (n=6), and the data showing significant difference ($p<0.05$) compared with those of control animals are marked with asterisks.

There was no difference in locomotory activity (exploratory behavior) on an open field between the animals with 75 mg/kg propofol-induced amnesia and the control animals at 5 minutes before the training (144.0±6.5 and 135.0±24.2 line crossing animals within 5 minutes in treated and control animals, respectively). There was also no difference 12 hours after the training and immediately before the memory regeneration test (110.6±4.9 and 119.3±13.0 line crossing animals within 5 minutes in treated and control animals, respectively). Therefore, it was not considered that the aforementioned amnesia condition was due to reduction of attention or motility.

Retrograde amnesia was induced by administering propofol 3 hours after the training. The induction of retrograde amnesia required a substantially larger dose of propofol (150 mg/kg), which resulted in complete loss of consciousness. Although the animals completely recovered consciousness 12 hours after the training and immediately before the memory regeneration test (no attentional or motile defect was observed on an open field; 158.0±25.8 and 163.0±13.5 line crossing animals within 5 minutes in the treated and control animals, respectively), the animals failed in memory regeneration 12 hours after the training (Table 1).

TABLE 1-1

| Treatment | Memory regeneration in anterograde amnesia (sec) |
| --- | --- |
| Control | 545 ± 33 |
| Propofol (10 mg/kg) | 454 ± 87 |
| Propofol (76 mg/kg) | 105 ± 38* |

*Significant difference was observed compared to animals with no treatment (control)

TABLE 1-2

| Treatment | Memory regeneration in retrograde amnesia (sec) |
| --- | --- |
| Control | 590 ± 7 |
| Propofol (100 mg/kg) | 554 ± 30 |
| Propofol (150 mg/kg) | 168 ± 93* |

*Significant difference was observed compared to animals with no treatment (control)

From the above results, it can be understood that the anesthetic action of propofol exhibited two characteristic features concerning the fixation of short term memory to long term storage. Even a relatively low concentration induced anterograde amnesia, whereas retrograde amnesia required a two-fold dose. The results indicate that memory trace is initially labile but becomes more robust with time.

Moreover, because administration of an aesthetically effective dose 4 hours after the training did not cause memory regeneration failure, it was considered that induction of retrograde amnesia by propofol was time-dependent. The results are shown in Table 2. In Table 2, the values are expressed as mean±standard error (n=6). The induction of retrograde amnesia was observed only within the first 3 hours after the training, and the result indicates that memory was incorporated in a process for final long-term storage after the duration. Animals administered with 150 mg/kg of propofol 6 hours after the training showed no attentional deficit and motility reduction in memory regeneration 12 hour after the training (88.7±9.4 and 92.3±13.1 line corssing animals within 5 minutes in treated and control animals, respectively).

TABLE 2

| Administration time of propofol (150 mg/kg) | Memory regeneration (sec) |
| --- | --- |
| 0 hour after training | 108 ± 10* |
| 1 hour after training | 183 ± 42* |
| 2 hours after training | 251 ± 86* |
| 3 hours after training | 210 ± 74* |
| 4 houxs after training | 541 ± 41* |
| 5 hours after training | 558 ± 29* |
| 6 hours after training | 471 ± 83* |

*Significant difference was observed compared to control animals with no treatment (567 ± 23 (sec))

Administration of nefiracetam (9 mg/kg) 1 hour before the training completely prevented anterograde amnesia induced by the treatment with propofol (75 mg/kg) 15 minutes before the training. No significant difference in reaction latency was observed between the control group and the group co-administered with propofol and nefiracetam, or the group administered with nefiracetam alone. Animals in which retrograde amnesia was induced with a high dose of propofol (150 mg/kg) also gave similar results. The results are shown in Table 3. The asterisks in Table 3 indicate that significant differences were observed compared to the group of sole administration of propofol (p<0.05). The values are expressed as mean±standard error (n=6).

TABLE 3-1

| Treatment | Memory regeneration in anterograde amnesia (sec) |
| --- | --- |
| Control | 535 ± 32 |
| Propofol (75 mg/kg) | 98 ± 18 |
| Nefiracetam (9 mg/kg) | 531 ± 68 |
| Propofol (75 mg/kg) + Nefiracetam (9 mg/kg) | 510 ± 90* |

*Significant difference was observed compared to animals administered with propofol (75 mg/kg) alone

TABLE 3-2

| Treatment | Memory regeneration in retrograde amnesia (sec) |
| --- | --- |
| Control | 568 ± 32 |
| Propofol (150 mg/kg) | 209 ± 74 |
| Nefiracetam (9 mg/kg) | 532 ± 68 |
| Propofol (150 mg/kg) + Nefiracetam (9 mg/kg) | 565 ± 22* |

*Significant difference was observed compared to animals administered with propofol (150 mg/kg) alone No difference in quality of anesthesia was observed between the group administered with propofol alone and the group co-administered with propofol and nefiracetam. The both groups showed similar reaction times in loss of tail pinch reaction and pedal withdrawal reflex (199.0±6.2 and 181.0±14.1 seconds in the group administered with propofol alone and the group co-administered with propofol and nefiracetam, respectively). Prolonged duration of the action was similar for the both groups as judged from recovery of righting reflex (96.3±12.7 and 90.3±10.5 minutes for the group administered with propofol alone and the group co-administered with propofol and nefiracetam, respectively).

Then, it was investigated whether or not nefiracetam protected learning-dependent modification of neuronal pollysialylation state in hippocampal dentate gyrus. As a control, frequency of generation of PSA positive neurons in the dentate gyrus was studied after induction of anterograde amnesia with propofol. As shown in Table 4-1, animals received passive avoidance reaction training exhibited marked increase of frequency of immune response-positive neurons, and significant increase in polysialylated cell number 12 hours after the training (Fox, G. B., et al., J. Neurochem., 65, pp. 2796–2799, 1995; Murphy, K. J., J. Neurochem, 67, pp. 1268–1274, 1996). The animals received induction of amnesia by administration of propofol (75 mg/kg) 15 minutes before the training showed no difference in number of polysialylated neurons as compared with animals immediately after the training, or untrained animals with no treatment.

On the other hand, the group received with co-administration (animals in which anterograde amnesia, induced by administration of propofol 15 minutes before the training, was prevented by the administration of nefiracetam 1 hour before the training) showed increase of polysialylated neurons at a similar level to that observed in the control group. Further, the learning-dependent increase of polysialylated neurons of hippocampal denate gyrus was also preserved in the animals in which retorgrade amnesia induced with propofol was prevented by the administration of nefiracetam. The results are shown in Table 4.

Because no significant difference in PSA-positive dentate gyrus neurons was observed between the untrained animals and untrained control animals 1 hour after the administration of nefiracetam (9 mg/kg) (69±3 and 64.5±2.3, respectively), it was observed that the increase in the expression of polysialylated neurons was not attributed only to the administration of nefiracetam

TABLE 4-1

| Treatment | Time (h) | Cell number per unit area (anterograde amnesia) |
|---|---|---|
| Untrained | — | 64.4 ± 3.9 |
| Control | 0 | 63.0 ± 4.5 |
| Control | 12 | 90.0 ± 7.8 |
| Propofol (75 mg/kg) | 12 | 57.0 ± 5.0 |
| Propofol (75 mg/kg) + Nefiracetam (9 mg/kg) | 12 | 83.0 ± 7.5* |

*Significant difference was observed compared to animals administered with propofol alone (75 mg/kg)

TABLE 4-2

| Treatment | Time (h) | Cell number per unit area (retrograde amnesia) |
|---|---|---|
| Untrained | — | 64.4 ± 3.9 |
| Control | 0 | 63.0 ± 4.5 |
| Control | 12 | 90.0 ± 7.8 |
| Propofol (150 mg/kg) | 12 | 66.0 ± 3.7 |
| Propofol (150 mg/kg) + Nefiracetam (9 mg/kg) | 12 | 103.0 ± 8.9* |

*Significant difference with respect to animals administered with propofol alone (150 mg/kg)

The medicament of the present invention is useful for preventive and/or therapeutic treatment of amnesia, in particular, preventive and/or therapeutic treatment of anterograde and/or retrograde amnesia caused by a general anesthetic agent.

What is claimed is:

1. A medicament for preventive and/or therapeutic treatment of amnesia caused by general anesthesia which comprises as an active ingredient N-(2,6-dimethyl-phenyl)-2-(2-oxo-1-pyrrolidinyl) acetamide in an effective amount for the preventive and/or therapeutic treatment of amnesia caused by general anesthesia.

2. The medicament according to claim 1, wherein the amnesia occurs after awakening from general anesthesia.

3. The medicament according to claim 1, wherein the amnesia is anterograde amnesia.

4. The medicament according to claim 1, wherein the amnesia is retrograde amnesia.

5. The medicament according to claim 1, wherein the general anesthesia is produced by an anesthetic agent for intravenous administration.

6. The medicament according to claim 1, wherein the general anesthesia is produced by an inhalation anesthetic agent.

7. A method for preventive and/or therapeutic treatment of amnesia caused by general anesthesia which comprises:

administering to a patent an amount of N-(2,6-dimethyl-phenyl)-2-(2-oxo-1-pyrrolidinyl) acetamide effective for the preventive and/or therapeutic treatment of amnesia.

8. The method according to claim 7, wherein the amnesia occurs after awakening from general anesthesia.

9. The method according to claim 7, wherein the amnesia is anterograde amnesia.

10. The method according to claim 7, wherein the amnesia is retrograde amnesia.

11. The method according to claim 7, wherein the general anesthesia is produced by an anesthetic agent for intravenous administration.

12. The method according to claim 7, wherein the general anesthesia is produced by an inhalation anesthetic agent.

13. A method for therapeutic treatment of amnesia caused by general anesthesia which comprises:

administering to a patent an amount of N-(2,6-dimethyl-phenyl)-2-(2-oxo-1-pyrrolidinyl) acetamide effective for the therapeutic treatment of amnesia.

14. The method according to claim 13, wherein the amnesia occurs after awakening from general anesthesia.

15. The method according to claim 13, wherein the amnesia is anterograde amnesia.

16. The method according to claim 13, wherein the amnesia is retrograde amnesia.

17. The method according to claim 13, wherein the general anesthesia is produced by an anesthetic agent for intravenous administration.

18. The method according to claim 13, wherein the general anesthesia is produced by an inhalation anesthetic agent.

* * * * *

UNITED STATES PATENT AND TRADEMARK OFFICE
CERTIFICATE OF CORRECTION

| | |
|---|---|
| PATENT NO. | : 6,281,242 B1 |
| DATED | : August 28, 2001 |
| INVENTOR(S) | : C. Regan et al. |

It is certified that error appears in the above-identified patent and that said Letters Patent is hereby corrected as shown below:

Title page,
Item [56], References Cited, under OTHER PUBLICATIONS, delete "Ogg, "Today's Treatment, Use of Anaesthesia, Implications of day-case surgery and Anaesthesia", Brit Med. J., 282, pp. 212-214 (1980)." (first occurrence) and insert -- Korttila, et al., "Randomized Comparison of Recovery after Propofol-Nitrous Oxide versus Thiopentone-Isoflurane-Nitrous Oxide Anaesthesia in Patients Undergoing Ambulatory Surgery," Acta Anaesthesiol Scand., 34, pp. 400-403 (1990). --

Signed and Sealed this

Twentieth Day of August, 2002

*Attest:*

*Attesting Officer*

JAMES E. ROGAN
*Director of the United States Patent and Trademark Office*